United States Patent [19]

Gregory et al.

[11] 4,056,575

[45] Nov. 1, 1977

[54] CHEMICAL PROCESS MAKING AROMATIC HYDROCARBONS OVER GALLIUM CATALYST

[75] Inventors: Reginald Gregory, Camberley; Alexander John Kolombos, Sutton, both of England

[73] Assignee: The British Petroleum Company Limited, London, England

[21] Appl. No.: 704,166

[22] Filed: July 12, 1976

[30] Foreign Application Priority Data

| July 17, 1975 | United Kingdom | 30012/75 |
| Nov. 20, 1975 | United Kingdom | 47829/75 |
| June 11, 1976 | United Kingdom | 24297/75 |

[51] Int. Cl.$^2$ .............................................. C07C 3/04
[52] U.S. Cl. ............................ 260/673.5; 208/135; 252/463; 260/673
[58] Field of Search ........................ 260/673.5, 673

[56] References Cited

U.S. PATENT DOCUMENTS

| 3,242,069 | 3/1966 | Gladrow et al. | 208/120 |
| 3,644,550 | 2/1972 | Beuther et al. | 260/673 |
| 3,702,886 | 11/1972 | Argauer et al. | 423/328 |
| 3,709,979 | 1/1973 | Chu | 423/328 |
| 3,764,515 | 10/1973 | Kiovsky | 208/10 |
| 3,770,616 | 11/1973 | Kominami et al. | 208/138 |
| 3,832,449 | 8/1974 | Rosinski et al. | 423/328 |
| 3,926,781 | 12/1975 | Gale | 208/117 |

*Primary Examiner*—Delbert E. Gantz
*Assistant Examiner*—G. E. Schmitkons
*Attorney, Agent, or Firm*—Brooks, Haidt, Haffner & Delahunty

[57] ABSTRACT

This invention relates to a process for aromatizing unsaturated hydrocarbons in the presence of a supported gallium catalyst. Xylenes may be prepared from $C_4$ feedstock by this route.

23 Claims, No Drawings

CHEMICAL PROCESS MAKING AROMATIC HYDROCARBONS OVER GALLIUM CATALYST

The present invention relates to a process for the production of aromatic hydrocarbons.

It has been known to use synthetic zeolites and/or aluminas as catalysts in the production of aromatic hydrocarbons from open chain hydrocarbons. However, the life of these catalysts have been short and the yield and selectivity of the cyclised products have been unsatisfactory due to severity of the reaction conditions needed to carry out the reaction.

It has now been found that by choosing a suitable metal as catalyst the activity over conventional catalysts may be increased significantly and acceptable yields of the aromatic hydrocarbons may be obtained under relatively moderate conditions.

Accordingly, the present invention is a process for producing aromatic hydrocarbons comprising aromatising an unsaturated hydrocarbon containing at least six carbon atoms in the presence of a catalyst composition comprising elemental gallium or a compound of gallium deposited on a support.

The unsaturated hydrocarbons of the present invention may be selected from one or more straight or branched chain isomers of hydrocarbons containing between 6 and 16 hydrocarbons. Methyl pentenes, dimethyl pentenes, trimethyl pentenes, hexenes, heptenes, and octenes are preferred.

Preferred examples of gallium compounds are gallium oxide, gallium sulphate and gallium ions exchanged by the surface hydroxyls of a surface active oxide such as hydrated silica or hydrated alumina.

The amount of gallium present in such catalyst compositions may vary between 0.01 and 10%, preferably between 0.1 and 6% by weight of the total support in the catalyst composition.

Suitable examples of support for the gallium/gallium compound catalysts of the present invention include aluminas such as eta-alumina, gamma-alumina and boehmite; aluminas and silica with or without surface hydroxyl groups which may be exchanged by ions of metals selected from gallium, aluminium, iron and/or nickel; activated carbon; and refractory gallium oxide. Silica supports especially those with exchanged surface hydroxyl groups are preferred.

The catalyst is prepared by impregnating the support with an aqueous solution of a soluble gallium compound, e.g. gallium nitrate. The paste so formed may be evaporated to dryness under vacuum and then pyrolysed at elevated temperature in a stream of air. Where it is desirable to use surface active silica or alumina as support, the hydroxyl groups may be exchanged by gallium ions.

The catalyst composition of the present invention may also contain other metals such as nickel, cobalt, iron, manganese, thallium, palladium, platinum, indium, germanium, chromium, tin and/or zinc in small quantities to improve the activity thereof. Nickel and nickel compounds are preferred.

The catalyst so prepared may be formed as a fixed bed and activated in the reactor tube itself. The activation may be carried out by purging the catalyst with a suitable gas such as nitrogen or air at the proposed reaction temperature.

The unsaturated hydrocarbon is thereafter aromatised by passing over the catalyst at a temperature between 400° and 750° C preferably between 500° and 600° C. The reaction is preferably carried out in an inert atmosphere. By "inert atmosphere" is meant a gas which is inert under the reaction conditions such as hydrogen or nitrogen.

The aromatisation reaction is suitably carried out under pressure ranging from 1 to 20 atmospheres, preferably from 1 to 5 atmospheres. The products of the reaction which are mainly aromatic hydrocarbons are then identified and isolated. Unsaturated $C_8$ hydrocarbons may be converted to xylenes by this process.

The unsaturated hydrocarbon being aromatised may be produced by the dimerisation of a lower olefin. For example, the $C_6$–$C_{16}$ unsaturated hydrocarbons to be aromatised may be prepared by the dimerisation of a $C_3$–$C_8$ mono olefin.

The dimerisation is suitably carried out over the same catalyst as that used for the cyclisation reaction, i.e. elemental gallium or a gallium compound deposited on a support.

The dimerisation is suitably carried out by passing the mono olefin hydrocarbon over the catalyst at a temperature between 20 and 300° C, preferably between 50° and 250° C. The reaction is preferably carried out in an atmosphere inert under the reaction conditions such as hydrogen or nitrogen.

The dimerisation of the mono olefin is suitably carried out at a reaction pressure ranging from atmospheric to 130 atmospheres, preferably between 3 atmospheres and 100 atmospheres.

The products of the dimerisation reaction may, without isolation, be directly subjected to the aromatisation reaction as before to obtain the aromatic products.

The mono olefinic hydrocarbons containing 3 to 8 carbon atoms may in turn be produced by the dehydrogenation of the corresponding saturated hydrocarbons.

The dehydrogenation of the saturated hydrocarbons to the corresponding olefin may be carried out by passing the saturated hydrocarbon over the same catalyst as used for dimerising the olefin and for the aromatisation of the unsaturated dimer thus produced. That is, the dehydrogenation may be carried out using a catalyst comprising elemental gallium or a compound of gallium deposited on a support. The types and compositions of the catalysts are the same as used before for the other reactions.

The saturated hydrocarbon is suitably passed over the gallium catalyst at a temperature of between 400° and 750° C, preferably between 500° and 600° C, to form the mono olefin.

At the lower end of the saturated hydrocarbon feedstock range higher temperatures may be required for the dehydrogenation step and conversely, as the number of carbon atoms in the feed increases, relatively lower temperatures within the specified range may be used to obtain optimum yields.

The dehydrogenation step is suitably carried at a reaction pressure of between 1 and 20 atmospheres, preferably between 1 and 5 atmospheres.

The dehydrogenation is also preferably carried out in an atmosphere inert under the reactions conditions, such as hydrogen. The hydrogen may be that liberated 'in situ' during the dehydrogenation reaction. The mono olefinic products may then be identified and isolated. This method may be used for producing propylenes from propane, butenes from n- and iso-butanes, pentenes from pentanes and so forth.

The dehydrogenated product may, without isolation, be directly dimerised and aromatised in one step to an aromatic compound. For example, propane may be dehydrogenated to propylene which may then be dimerised and aromatised in one step to benzene. Similarly, isobutane may be dehydrogenated to isobutene which can be dimerised and aromatised to xylenes.

The dehydrogenation, dimerisation and aromatisation reactions may proceed simultaneously and the product mix may be controlled by careful control of reaction conditions. That is, for a given feedstock, the dehydrogenation normally proceeds at the lower end of the specified temperature range whereas the dehydrocyclodimerisation reaction to the corresponding aromatic hydrocarbon predominates at the upper end of the same temperature range.

The principal advantage of the present process is that the steps of the dehydrogenation, dimerisation and aromatisation can all be carried out using the same catalyst. That is, the saturated hydrocarbon can be converted to the aromatic product using a single set of reaction conditions over a single catalyst. Furthermore, one can start with a mixed feed containing both saturated and unsaturated hydrocarbons and convert the mixture into the desired aromatic product in a single step. Thus, a $C_4$ feedstock containing one or more of butanes, butenes and butadienes may be converted into xylenes in a single reactor without isolating the intermediates.

The invention is further illustrated with reference to the accompanying examples.

Preparation of 6% $Ga_2O_3$/Eta-alumina catalyst

To a solution of 10 g gallium nitrate ($Ga(NO_3)_3.8H_2O$) in approximately 30 ml of distilled water, 26.6 g eta-alumina was added and stirred into a paste. The paste was evaporated to dryness in a vacuum oven overnight and heated in air at 550° for six hours to give gallium oxide (6% wt. gallium) on eta-alumina.

4.9 g gallium nitrate, $Ga(NO_3)_3$, $8H_2O$, dissolved in 15 ml distilled water was added to 13 g Crosfields U 40 silica suspended in 15 ml distilled water. The mixture was evaporated to dryness in a vacuum oven overnight and heated in air at 550° for six hours to give gallium oxide (6% wt. gallium) on silica.

Preparation of gallium exchanged silica catalyst 400 g of Crosfields U 40 silica gel was hydrolysed by standing under 1 l distilled water for 3 days. The silica gel was decanted dry and stood under 4 l of 2N nitric acid for 6 hours, and then finally washed with 12 l of distilled water in a Buchner funnel. The silica gel was dried at 200° C for 72 hours and calcined at 500° C in air for 72 hours.

4.5 g of gallium nitrate, $Ga(NO_3)_3$, $9H_2O$, was dissolved in 200 ml of distilled water. 30 ml of the prepared silica gel was packed into a glass column and the gallium nitrate solution was percolated through the column for 18 hours. The catalyst was finally washed with 1500 ml of distilled water and dried in a vacuum oven overnight. The gallium exchanged silica catalyst (0.6% wt. gallium) was heated in air at 550° C for 6 hours before use.

Similarly catalysts containing higher percentage of gallium (e.g. 1.8% wt. Ga) were prepared by exchanging further quantities of gallium nitrate under controlled pH conditions.

Preparation of $Ga_2O_3$/silica catalyst 4.9 g gallium nitrate, $Ga(NO_3)_3$, $8H_2O$ dissolved in 15 ml distilled water was added to 13 g Crosfields U 40 silica suspended in 15 ml distilled water. The mixture was evaporated to dryness in a vacuum oven overnight and heated in air at 550° for six hours to give gallium oxide (6% wt. gallium) on silica.

EXAMPLE 1

When di-isobutene was passed over a gallium exchanged silica catalyst (1.8% wt. gallium) at a reaction temperature of 600° C at 5.1 sec. residence time, 99.8% of the di-isobutene was converted. The major products (expressed as percent weight yield) were $C_1$-$C_3$ hydrocarbons (14.9%), $C_4$ hydrocarbons (48.7%) and aromatics (32.7%). Xylenes made up 22.8% weight yield of the aromatics.

EXAMPLE 2

When isobutene was passed over a gallium oxide (6% wt. gallium)/eta-alumina catalyst at a reaction temperature of 550° C and a residence time of 5.5 sec. after 1.5 minutes on stream 96.3% of the isobutene was converted. The major products (expressed as percent weight yield) were butenes (7.5%), butanes (15%), $C_1$-$C_3$ hydrocarbons (26.6%) and aromatics (47%). Xylenes made up 25.7% weight yield of the aromatics. With total $C_4$'s recycle the selectivity to aromatics is 60.6% and to xylenes 33.2%.

EXAMPLE 3

The catalyst of Example 2 was reactivated in air at 550° C and under similar conditions to Example 1 but after 10 minutes on stream gave 88.7% conversion of isobutene. The major products (expressed as percent weight yield) were butenes (21.8%), butanes (22.8%), $C_1$-$C_3$ hydrocarbons (19.7%), and aromatics (28.1%). Xylenes made up 15.3% weight yield of the aromatics. With total $C_4$'s recycle the selectivity to aromatics is 50.7% and to xylenes 27.6%.

EXAMPLE 4

When isobutene was passed over a gallium oxide (6% wt. gallium) on silica catalyst at a reaction temperature of 550° and a residence time of 5.9 sec., after 1.5 minutes on stream 49.1% of the isobutene was converted. The major products (expressed as percent weight yield) were butenes (66.7%), butanes (7.2%), $C_1$-$C_3$ hydrocarbons (4.6%), and aromatics (16.4%). Xylenes made up 11.8% weight yield of the aromatics. With total $C_4$'s recycle the selectivity to aromatics is 63.3% and to xylenes 45.4%. The activity was unchanged after 1 hour on stream.

EXAMPLE 5

When isobutane was passed over a gallium oxide (6% wt. gallium) on silica catalyst at a reaction temperature of 590° and a residence time of 6.2 sec., after 2.5 minutes on stream 65.1% of isobutane was converted. The major products (expressed as percent weight yield) were butanes (39.3%), butenes (38.7%), $C_1$-$C_3$ hydrocarbons (9.4%), and aromatics (9.2%). Xylenes made up 6.5% weight yield of the aromatics. With total $C_4$'s recycle the selectivity to aromatics is 42.4% and to xylenes 29.9%. The activity was unchanged after one hour on stream.

EXAMPLE 6

In this example the support was a silica containing surface hydroxyl groups exchanged with aluminium ions.

When isobutene was passed over gallium oxide (3% wt. gallium)/aluminium (0.8% wt.)/silica catalyst at a reaction temperature of 600° C and a residence time of 6.3 seconds, after 2.5 minutes on stream 72.9% of the isobutene was converted. The major products (expressed as percent weight yield) were butenes (46.5%), butanes (8.7%), $C_1$–$C_3$ hydrocarbons (14.4%) and aromatics (23%). Xylenes made up 14.6% weight yield of the aromatics and with total $C_4$'s recycle at constant activity, the selectivity to aromatics was 51.5% and to xylenes 32.7%.

EXAMPLE 7

When propylene was passed over the gallium exchanged silica catalyst (0.6% wt. gallium) at a reaction temperature of 650° and a residence time of 5.2 sec., after 2.5 minutes on stream 50% of propylene was converted. The major products were $C_1$–$C_3$ hydrocarbons, 23.5% wt., and aromatics 21.1% wt. Benzene made up 9.9% wt. yield of the aromatics. With total propylene recycle the selectivity to aromatics is 42.2% and to benzene 19.8%.

EXAMPLE 8

When isobutene was passed over the gallium exchanged silica catalyst (0.6% wt. gallium) at a reaction temperature of 600° C and a residence time of 6 sec. after 2.5 minutes on stream 74.9% of isobutene was converted. The major products (expressed as percent weight yield) were butenes (35%), butanes (4.8%), $C_1$–$C_3$ hydrocarbons (8.3%), and aromatics (25%). Xylenes made up 18.6% weight yield of the aromatics. With total $C_4$'s recycle the selectivity to aromatics is 75% and to xylenes 53.3%. The activity was unchanged after one hour on stream.

EXAMPLE 9

When 3-methylbutene-1 was passed over the gallium exchanged silica catalyst (0.6% wt. gallium) at a reaction temperature of 650° C at 6 sec. residence time, after 15 minutes on stream 97.3% of 3-methylbutene-1 was converted. The major products (expressed as percent weight yield) were $C_1$–$C_3$ hydrocarbons (33.8%), $C_4$ hydrocarbons (7.2%) and aromatics (39.9%).

EXAMPLE 10

An isobutene feed was passed over a gallium (1.8% wt. Ga) exchanged silica catalyst at atmospheric pressure, a temperature of 200° C and a contact time of 10.5 seconds. 67.8% of the isobutene fed was converted to give 43.8% wt. of open chain $C_8$ isomers and 14.4% wt. of open chain $C_{12}$ isomers.

EXAMPLE 11

Using the same catalyst as Example 10 above but using 3-methyl-butene-1 as feed and a contact time of 11.7 seconds, 6.2% wt. (59.6% selectivity) of open chain $C_{10}$ isomers were formed.

We claim:

1. A process for the production of aromatic hydrocarbons comprising subjecting an unsaturated hydrocarbon containing at least six carbon atoms to aromatisation in the presence of a catalyst consisting essentially of elemental gallium or a compound of gallium deposited on a support.

2. A process for producing aromatic hydrocarbons according to claim 1 wherein the unsaturated hydrocarbon starting material is produced by dimerising a $C_3$–$C_8$ mono-olefin in the presence of the aromatisation catalyst.

3. A process for the production of aromatic hydrocarbons from an unsaturated hydrocarbon produced by the dimerisation of a mono-olefin according to claim 2 wherein the mono-olefin is produced by the dehydrogenation of a $C_3$–$C_8$ saturated hydrocarbon in the presence of the aromatisation catalyst.

4. A process according to claim 1 wherein the unsaturated hydrocarbon has between 6 and 16 carbon atoms.

5. A process according to claim 1 wherein the gallium compound comprising the aromatisation catalyst is selected from gallium oxide, gallium sulphate and gallium ions exchanged with the surface hydroxyl groups of a surface active oxide selected from hydrated alumina and hydrated silica.

6. A process according to claim 1 wherein the catalyst support is selected from an alumina, a silica, activated carbon and refractory gallium oxide.

7. A process according to claim 6 wherein the alumina is selected from eta-alumina, gamma-alumina and boehmite.

8. A process according to claim 6 wherein the alumina and silica have surface hydroxyl groups.

9. A process according to claim 8 wherein the surface hydroxyl groups are exchanged by ions of one or more metals selected from gallium, aluminium, iron and nickel.

10. A process according to claim 1 wherein the aromatisation is carried out at a temperature between 400° and 750° C.

11. A process according to claim 1 wherein the cyclisation is carried out at a reaction pressure of between 1 and 20 atmospheres.

12. A process according to claim 1 wherein the aromatisation is carried out in an atmosphere inert under the reaction conditions selected from hydrogen and nitrogen.

13. A process according to claim 2 wherein the mono-olefin being dimerised is selected from propylene, butenes, pentenes and mixtures thereof.

14. A process according to claim 2 wherein the dimerisation of the mono-olefin is carried out at a temperature between 20° and 300° C.

15. A process according to claim 2 wherein the dimerisation of the mono-olefin is carried out at a reaction pressure of between 1 and 130 atmospheres.

16. A process according to claim 2 wherein the dimerisation is carried out in an atmosphere inert under the reaction conditions selected from hydrogen and nitrogen.

17. A process according to claim 3 wherein the feedstock contains one or more hydrocarbons selected from propane, butane, isobutane and pentane.

18. A process according to claim 3 wherein the dehydrogenation is carried out at a temperature between 400° and 750° C.

19. A process according to claim 3 wherein the dehydrogenation is carried out at a pressure of between 1 and 20 atmospheres.

20. A process for producing xylenes directly from a $C_4$ feedstock containing one or more of butanes, butenes and butadiene by passing the feedstock over an aromatisation catalyst consisting essentially of elemental gallium or a gallium compound deposited on a support at a temperature between 400° and 700° C and a pressure between 1 and 20 atmospheres.

21. A process for the production of aromatic hydrocarbons comprising subjecting an unsaturated hydrocarbon containing at least six carbon atoms to aromatisation in the presence of a catalyst consisting essentially of (a) elemental gallium or a compound of gallium, and (b) one or more of the metals nickel, cobalt, iron, manganese, thallium, palladium, platinum, indium, germanium, chromium, tin, and zinc deposited on a support.

22. A process as defined in claim 21 wherein the mono-olefin is produced by the dehydrogenation of a $C_3-C_8$ saturated hydrocarbon in the presence of the aromatisation catalyst.

23. A process for producing xylenes directly from a $C_4$ feedstock containing one or more of butanes, butenes and butadiene by passing the feedstock over an aromatisation catalyst consisting essentially of (a) elemental gallium or a gallium compound, and (b) one or more of the metals nickel, cobalt, iron, manganese, thallium, palladium, platinum, indium, germanium, chromium, tin and zinc deposited on a support.

* * * * *